(12) United States Patent
Levin et al.

(10) Patent No.: US 8,406,875 B2
(45) Date of Patent: Mar. 26, 2013

(54) ROUTING OF PACING SIGNALS

(75) Inventors: Michael Levin, Haifa (IL); Avi Reuveni, Givat-Shmoel (IL); Yoav Lichtenstein, Raanana (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 34 days.

(21) Appl. No.: 12/914,199

(22) Filed: Oct. 28, 2010

(65) Prior Publication Data

US 2012/0109242 A1 May 3, 2012

(51) Int. Cl.
*A61N 1/362* (2006.01)
(52) U.S. Cl. .......................................... 607/10; 600/510
(58) Field of Classification Search ................. 607/9, 10; 606/34, 42; 600/510
See application file for complete search history.

(56) References Cited

U.S. PATENT DOCUMENTS

| | | | |
|---|---|---|---|
| 4,579,119 A | 4/1986 | Callaghan | |
| 5,391,199 A | 2/1995 | Ben-Haim | |
| 5,431,692 A | 7/1995 | Hansen et al. | |
| 5,813,991 A * | 9/1998 | Willis et al. | 600/510 |
| 6,101,410 A | 8/2000 | Panescu et al. | |
| 6,239,724 B1 | 5/2001 | Doron et al. | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 7,252,664 B2 | 8/2007 | Nasab et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2008/0281312 A1 | 11/2008 | Werneth et al. | |

FOREIGN PATENT DOCUMENTS

| | | |
|---|---|---|
| WO | WO 94/10904 A1 | 5/1994 |
| WO | WO 96/05768 A1 | 2/1996 |
| WO | WO 97/06729 A1 | 2/1997 |
| WO | WO 2010/058350 A1 | 5/2010 |

OTHER PUBLICATIONS

McLaughlin, N.B. Review of Seven Cardiac Electrophysiology Stimulators. Physiological Measurement, vol. 14, No. 1, Feb. 1993 Abstract.

McLaughlin, N.B. Review of Seven Cardiac Electrophysiology Stimulators. Physiological Measurement, vol. 14, No. 1, pp. 57-69, Feb. 1993.

Extended European Search Report dated Jan. 31, 2012 from related European Application No. 11186820.4.

* cited by examiner

*Primary Examiner* — George Evanisko
(74) *Attorney, Agent, or Firm* — Louis J. Capezzuto

(57) ABSTRACT

An apparatus includes a sensing unit and control circuitry. The sensing unit is connected to a channel that delivers Electro-Physiological (EP) signals from a cardiac catheter to an EP recording system and pacing signals from the EP recording system to the catheter. The sensing unit is configured to automatically identify time intervals during which the pacing signals are delivered. The control circuitry is configured to route the EP signals on the channel from the catheter to the EP recording system via an intervening system that is detrimental to the pacing signals, to switch the channel to an alternate path that bypasses the intervening system during the identified time intervals, and to route the pacing signals from the EP recording system to the cardiac catheter over the alternate path.

16 Claims, 2 Drawing Sheets

ROUTING OF PACING SIGNALS

FIELD OF THE INVENTION

The present invention relates generally to medical probes, and particularly to methods and systems for routing of signals to and from medical probes.

BACKGROUND OF THE INVENTION

Cardiac Electro-Physiological (EP) study procedures involve sensing and recording EP signals from a patient's heart, e.g., using a cardiac catheter. In some EP study procedures, the patient's heart is paced by applying pacing signals. EP study is sometimes carried out in conjunction with an ablation procedure, in which ablation signals are applied to a certain region on the heart's surface.

Several methods and systems for coordinating EP signals, pacing signals and/or ablation signals during such procedures are known in the art. For example, PCT International Publication WO 1997/06729, whose disclosure is incorporated herein by reference, describes an EP system that includes an amplification system, an ablation machine, a filter box, a display monitor and a chart recorder. The amplification system receives endocardial signals from an ablation catheter during both an EP study and an ablation procedure. The amplification system, ablation machine and ablation catheter are interconnected with the filter box such that the endocardial signals and the high energy ablation signal pass therethrough and are filtered thereby.

PCT International Publication WO 1994/10904, whose disclosure is incorporated herein by reference, describes an ablation catheter, which has an ablation electrode at its distal end coupled to an ablation power source through low-impedance coupling. The ablation electrode also functions as a sensing electrode for monitoring an endocardial signal and preferably also tissue impedance during an ablation procedure. The ablation electrode is coupled to an electrode monitor through high-impedance coupling. A timing element operates a plurality of switches to selectively isolate, dampen or interconnect various signal paths during plural repetitive non-overlapping ablation and quiescent intervals. RF energy is delivered to the ablation site during the ablation intervals. The local endocardial signal is measured during the quiescent intervals.

U.S. Patent Application Publication 2008/0281312, whose disclosure is incorporated herein by reference, describes an ablation therapy system, which includes a Multi-Channel RF Ablation Generator, an ECG interface, an assembly of at least three ablation catheters and an ECG interface operably coupling and interfacing the catheters to both an ECG unit and the RF Ablation Generator.

SUMMARY OF THE INVENTION

An embodiment of the present invention that is described herein provides an apparatus, including:

a sensing unit, which is connected to a channel that delivers Electro-Physiological (EP) signals from a cardiac catheter to an EP recording system and pacing signals from the EP recording system to the catheter, and which is configured to automatically identify time intervals during which the pacing signals are delivered; and control circuitry, which is configured to route the EP signals on the channel from the catheter to the EP recording system via an intervening system that is detrimental to the pacing signals, to switch the channel to an alternate path that bypasses the intervening system during the identified time intervals, and to route the pacing signals from the EP recording system to the cardiac catheter over the alternate path.

In some embodiments, the sensing unit is configured to identify the time intervals by sensing the pacing pulses delivered on the channel. In an embodiment, the sensing unit is configured to cause the control circuitry to route the pacing signals over the alternate path responsively to sensing the pacing signals on the channel, and to cause the control circuitry to route the EP signals via the intervening system responsively to sensing that the pacing signals are not present on the channel.

In a disclosed embodiment, the control circuitry includes one or more switches that are controlled by the sensing unit in order to switch the channel. In an example embodiment, the one or more switches include first and second switches, and the sensing unit is configured to route the pacing signals over the alternate path by opening the first switch and closing the second switch, and to route the EP signals via the intervening system by closing the first switch and opening the second switch. In another embodiment, the pacing signals include pulses having a given pulse width, and the one or more switches have a switching time that does not exceed 10% of the given pulse width. In yet another embodiment, the intervening system includes a position tracking system that measures a position of the cardiac catheter.

There is additionally provided, in accordance with an embodiment of the present invention, a method, including:

in a system that includes a cardiac catheter that is connected to an Electro-Physiological (EP) recording system by a channel, routing the EP signals on the channel from the catheter to the EP recording system via an intervening system that is detrimental to the pacing signals;

automatically identifying time intervals during which the pacing signals are delivered;

switching the channel to an alternate path that bypasses the intervening system during the identified time intervals; and routing the pacing signals from the EP recording system to the cardiac catheter over the alternate path.

The present invention will be more fully understood from the following detailed description of the embodiments thereof, taken together with the drawings in which:

DETAILED DESCRIPTION OF EMBODIMENTS

Overview

Figure 1:
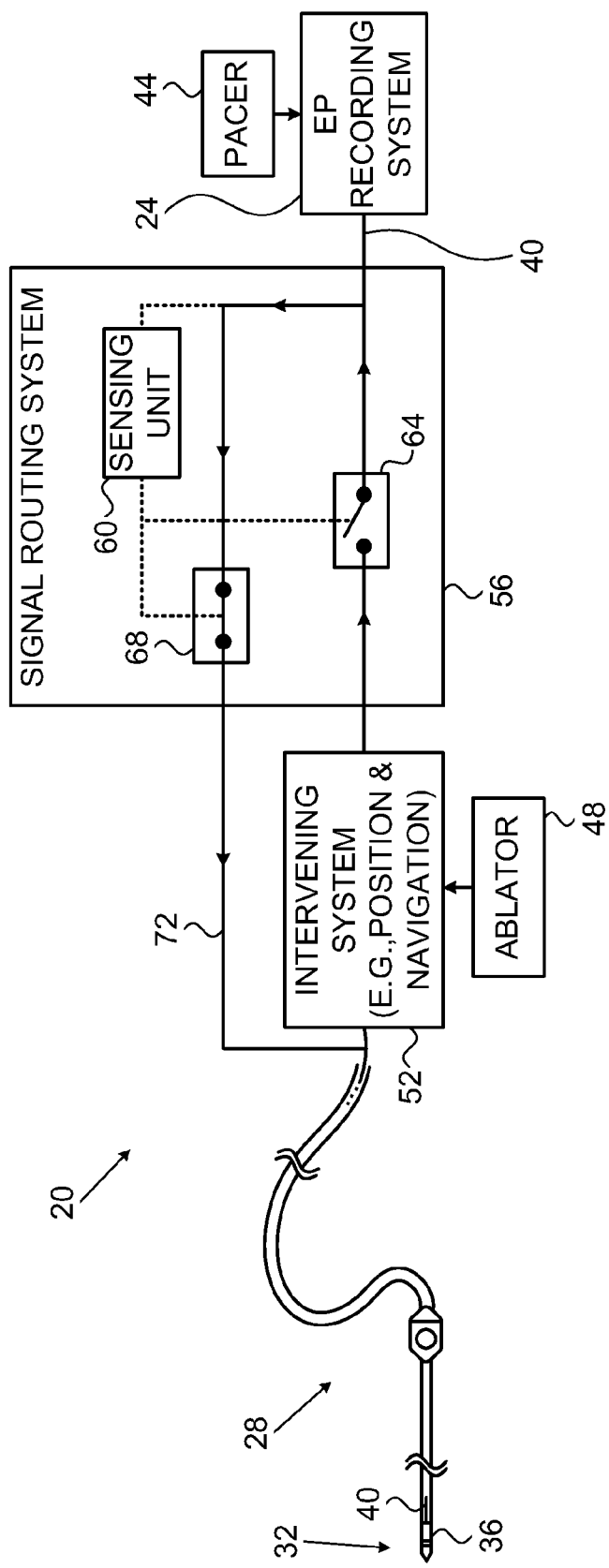
FIG. 1 is a block diagram that schematically illustrates a system for EP study, pacing and ablation, in accordance with an embodiment of the present invention.

In a typical EP study procedure, a physician navigates a catheter in a patient's cardiac chamber in order to map the electrical potentials on the endocardial surface. The catheter is fitted with one or more electrodes, which come into contact with the surface and produce EP signals that are indicative of the local electrical potential. The EP signals are delivered from the catheter over a channel (e.g., cable connection) to an EP recording system, which records and presents the sensed electrical potentials to the physician. In some cases, the EP study procedure also involves pacing the patient's heart by delivering pacing signals over the channel from the EP recording system to the catheter electrodes.

In some system configurations, the channel between the catheter and the EP recording system traverses an intervening system, such as a position tracking system that measures and displays the catheter position in the heart. The intervening system is typically designed to allow the EP signals generated by the catheter to pass through with little or no degradation en-route to the EP recording system. In the opposite direction, however, the intervening system often blocks or distorts the pacing signals delivered from the EP recording system to the catheter.

Embodiments of the present invention that are described hereinbelow provide improved methods and systems for routing EP signals and pacing signals between an EP recording system and a catheter. In some embodiments, the channel between the catheter and the EP recording system has two paths—a direct path that traverses the intervening system, and an alternate path that bypasses the intervening system. A signal routing system alternates between the two paths. In some embodiments, the signal routing system automatically identifies time intervals during which the pacing signals are transmitted from the EP recording system, e.g., by sensing the pacing signals on the cable connection. Based on the identified time intervals, the signal routing system selects whether to connect the EP recording system and the catheter via the direct path or via the alternate path.

Typically, the signal routing system selects the alternate path during the identified time intervals and the direct path otherwise. Thus, the pacing signals are routed over the alternate path and are not blocked or distorted by the intervening system. Outside the identified time intervals, the EP signals are routed over the direct path via the intervening system, so that the intervening system can make use of these signals.

The methods and systems described herein enable the EP recording system and the intervening system to co-exist, while allowing uninterrupted delivery of EP signals and pacing signals. Since the entire switching process is performed automatically, the process is transparent to the physician, who may apply pacing whenever desired. The disclosed techniques also simplify compliance with hospital regulations that require continuous monitoring of EP signals during EP study procedures.

System Description

FIG. 1 is a block diagram that schematically illustrates a system 20 for EP study, pacing and ablation, in accordance with an embodiment of the present invention. System 20 comprises an EP recording system 24, which is connected to a cardiac catheter 28 that is inserted into a patient's cardiac chamber. A distal tip 32 of catheter 28 comprises one or more electrodes 36. Electrodes 36 may be used for EP sensing (sensing of local electrical potential), pacing and/or ablation. In some embodiments, each function (EP sensing, pacing, ablation) is carried out by a separate electrode. Alternatively, a given electrode may be used for performing two or more of these functions, e.g., EP sensing and pacing.

EP recording system 24 is connected to electrodes 36 of catheter 28 using a signal channel. In the embodiments described herein, the channel comprises a cable connection 40. Generally, however, the channel may comprise, at least in part, any other suitable connection that allows signal delivery between the catheter electrodes and the EP recording system. The channel may comprise, for example, connectors, circuit traces or any other suitable connection types. In some embodiments, the channel is also used for connecting to body-surface electrocardiogram (ECG) electrodes attached to the patient.

EP recording system 24 receives from catheter 28 EP signals, which are indicative of the local electrical potential that is sensed by electrodes 36. The EP recording system typically presents the sensed electrical potentials to a physician as part of an EP study procedure. EP recording system 24 may also record the sensed electrical potentials for later analysis. EP recording systems that can be used as part of system 20 comprise, for example, systems offered by GE Healthcare, Siemens AG, or any other suitable system.

In some embodiments, a pacer 44 is connected to EP recording system 24. Pacer 44 generates pacing signals (also referred to as pacing pulses) for application to the patient's heart by electrodes 36 of catheter 28. Any suitable pacer can be used for this purpose, such as, for example, the UHS 3000 Heart Stimulator produced by BioTronik, the EPS320 Cardiac Stimulator produced by Micropace EP, Inc. (Santa Anna, Calif.), or the Bloom EP Stimulators offered by Fischer Medical Technologies, Inc. (Broomfield, Colo.). Several additional cardiac stimulators that can be used for this purpose are described in an article by McLaughlin et al., entitled "Review of Seven Cardiac Electrophysiology Stimulators," Physiological Measurement, volume 14, no. 1, February, 1993, which is incorporated herein by reference. The pacing signals produced by pacer 44 are delivered from EP recording system 24 to catheter 28 over cable connection 40.

In some embodiments, system 20 comprises an ablator 48. The ablator produces ablation AC current signals that are also delivered to the catheter. The present description, however, is focused primarily on EP signals and pacing signals. Handling of ablation AC current signals is considered outside the scope of the present disclosure.

In some embodiments, cable connection 40 (or other channel) traverses an intervening system 52 between catheter 28 and EP recording system 24. In the present embodiment, the intervening system comprises a position tracking and navigation system that measures the position coordinates of the catheter in the patient's heart and displays the measured position to the physician. An example of such a system is the CARTO™ system, produced by Biosense-Webster Inc. (Diamond Bar, Calif.). Position tracking schemes of this sort are described, for example, in U.S. Pat. Nos. 5,391,199, 6,690, 963, 6,484,118, 6,239,724, 6,618,612 and 6,332,089, in PCT International Publication WO 1996/005768, and in U.S. Patent Application Publications 2002/0065455 A1, 2003/0120150 A1 and 2004/0068178 A1, whose disclosures are all incorporated herein by reference. Alternatively, however, the disclosed techniques can be used with any other suitable intervening system.

Typically, the intervening system makes use of the catheter electrodes, and in particular the EP signals. Therefore, the channel should not bypass the intervening system completely at all times. In the CARTO system mentioned above, for example, the EP signals are used to create electroanatomical maps that are displayed to the physician. In some cases the intervening system may use the catheter electrodes for impedance-based position measurements.

Intervening system 52 (position tracking system in the present example) is designed to allow the EP signals to pass from its input to its output (i.e., from the catheter en-route to the EP recording system) with little or no degradation. In particular, the position tracking system may filter the EP signals traversing it, so as to retain the purity of the EP signals and suppress interfering signals and noise. In the opposite direction (from the EP recording system to the catheter), on the other hand, the intervening system often blocks or distorts the signals. As such, if system 20 were to attempt passing the pacing signals (from the EP recording system en-route to the catheter) through the intervening system, the pacing signals would have been blocked or distorted.

In order to avoid distortion or blockage of the pacing signals, system 20 comprises a signal routing system 56, which routes the pacing signals over a path that bypasses intervening system 52. This bypassing operation is performed without compromising the delivery of EP signals from the catheter to the EP recording system. In some embodiments, cable connection 40 (or other channel) has two paths that connect catheter 28 with EP recording system 24—a direct path that traverses intervening system 52, and an alternate path 72 that bypasses the intervening system. Signal routing system 56 alternates between the two paths depending on whether a pacing signal is present or not.

Routing system 56 comprises a sensing unit 60, which identifies time intervals in which pacing signals are transmitted from EP recording system 24 to catheter 24. In an example embodiment, unit 60 senses the signal channel (e.g., cable connection 40) and detects the presence or absence of a pacing signal. Alternatively, unit 60 may identify the time intervals using any other suitable method. Based on the identified time intervals, control circuitry in system 56 selects one of the paths of the signal channel for connecting the EP recording system and the catheter.

In the embodiment of FIG. 1, the control circuitry comprises a switch 64 and a switch 68, both controlled by sensing unit 60. The switches may comprise, for example, Metal Oxide Semiconductor Field Effect Transistor (MOSFET) switches, or any other suitable type of switch. By setting switches 64 and 68, sensing unit 60 can choose whether to connect the EP recording system to the catheter over the direct path or over the alternate path.

When switch 64 is closed and switch 68 is open, EP recording system 24 is connected to catheter 28 over the direct path that traverses intervening system 52. Sensing unit 60 applies this switch setting outside the identified time intervals, i.e., when a pacing signal is not detected and EP signals are to be transferred from the catheter to the EP recording system via the intervening system.

When switch 64 is open and switch 68 is closed (the setting shown in the figure), EP recording system 24 is connected to catheter 28 over alternate path 72 that bypasses intervening system 52. Sensing unit 60 applies this switch setting during the identified time intervals, i.e., when a pacing signal is detected and is to be delivered from the EP recording system to the catheter. As a result, the pacing signal is delivered without blockage or distortion caused by the intervening system.

Typically, the pacing signal comprises a sequence of pacing pulses. In response to such a pacing signal, sensing unit toggles the setting of switches 64 and 68 in alternation, such that the alternate (bypassing) path is selected during the pacing pulses, and the direct path is selected between the pacing pulses.

The configurations of system 20 and system 56 in FIG. 1 are example configurations, which are chosen purely for the sake of conceptual clarity. In alternative embodiments, any other suitable configurations can also be used. The example of FIG. 1 illustrates a single signal channel, i.e., a single line between a catheter and the EP recording system that delivers a single EP signal and a single pacing signal. Real-life EP recording systems typically comprise multiple signal channels, e.g., between four and twenty catheter electrodes per catheter (and often using more than one catheter) and ten body-surface ECG electrodes. Alternatively, any other suitable numbers of channels can be used. In some embodiments, signal routing system 56 comprises multiple direct paths and multiple alternate paths, e.g., a respective pair of direct path and alternate path for each signal channel. In these embodiments, sensing unit switches between the direct and alternate paths of each channel independently, according to the pacing signal on that channel.

Signal routing system 56 can be implemented using discrete components, or in an Application-Specific Integrated Circuit (ASIC) or Field-Programmable Gate Array (FPGA). Some of the functions of system 56 can be implemented in software. In some embodiments, the functions of signal routing system 56 can be embedded in one of the other elements of system 20, e.g., as part of the intervening system.

Figure 2:
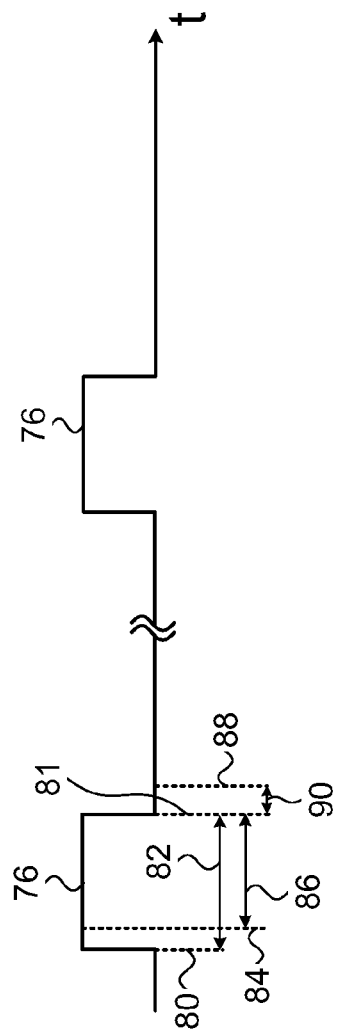
FIG. 2 is a timing diagram showing pacing signals routed over a cable connection, in accordance with an embodiment of the present invention.

FIG. 2 is a timing diagram showing pacing signals routed over cable connection 40, in accordance with an embodiment of the present invention. The figure illustrates the effect of the finite switching time of switches 64 and 68, and the response time of sensing unit (i.e., the time from appearance of a pacing pulse on cable connection 40 until unit 60 sends control signals that toggle switches 64 and 68 in response to the pulse). In a typical implementation, the width of each pacing pulse is between 1-3 ms. The response time of the sensing unit and the switching times of the switches are typically considerably shorter than the width of the pacing pulses, e.g., on the order of several microseconds. In some embodiments, however, the system comprises filters for decreasing sensitivity to ablation frequencies. In such embodiments, the sensing and switching time may increase to several tens of microseconds, e.g., between 20-50 μs. These numerical values are given purely by way of example, and any other suitable values can be used in alternative embodiments.

The figure shows pacing pulses 76 that are delivered from EP recording system 24 to catheter 28. Each pacing pulse 76 has a pulse width 82. The leading edge of the pacing pulse appears on the cable at a time 80. Because of the response time of sensing unit 60 and the switching time of switches 64 and 68, the alternate (bypassing) path may be set up only at a time 84, which is slightly later than time 80. Thus, the pacing pulse that is actually delivered to catheter 28 has a pulse width 86 that is slightly narrower than the original pulse width 82. In the present example, the original pulse width 84 is between 1-4 ms, and the narrower pulse width is between 0.95-3.95 ms. This sort of degradation is usually tolerable. In many cases, the physician can compensate for the loss of pacing pulse energy by increasing the pacing pulse amplitude using pacer 44.

The falling edge of pacing pulse 76 on cable connection 40 occurs at a time 81. Because of the sensing unit response time and the switching time of the switches, the direct path (via the intervening system) may be connected only at a time 88. As a result, the EP recording system may not receive EP signals from the catheter during an interval 90, even though the actual pacing pulse has already ended. (Note that the EP recording system does not receive EP signals during the entire pulse width 82 and an additional short period of time, e.g., >20 ms, needed for the EP recording system to recover from the saturation caused by the pacing pulses. The finite switching times extend this time period by interval 90, which is much shorter than the recovery time of the EP recording system.) In the present example, pulse width 86 is between 0.95-3.95 ms, and the length of interval 90 is between 1.05-4.05 ms. Since interval 90 is shorter than the recovery time of the EP recording system, no degradation is caused.

Typically, the switching time of the switches is considerably smaller than the pulse width of the pacing signals, so that the loss of energy is small. In a typical embodiment, the switching time does not exceed 10% of the pacing pulse width for a 1 ms pacing pulse, no more than 5% for a 2 ms pacing pulse, and so on. The description above is given purely by way of example. In alternative embodiments, any other suitable pulse widths and delays can be used.

Signal Routing Method Description

Figure 3:
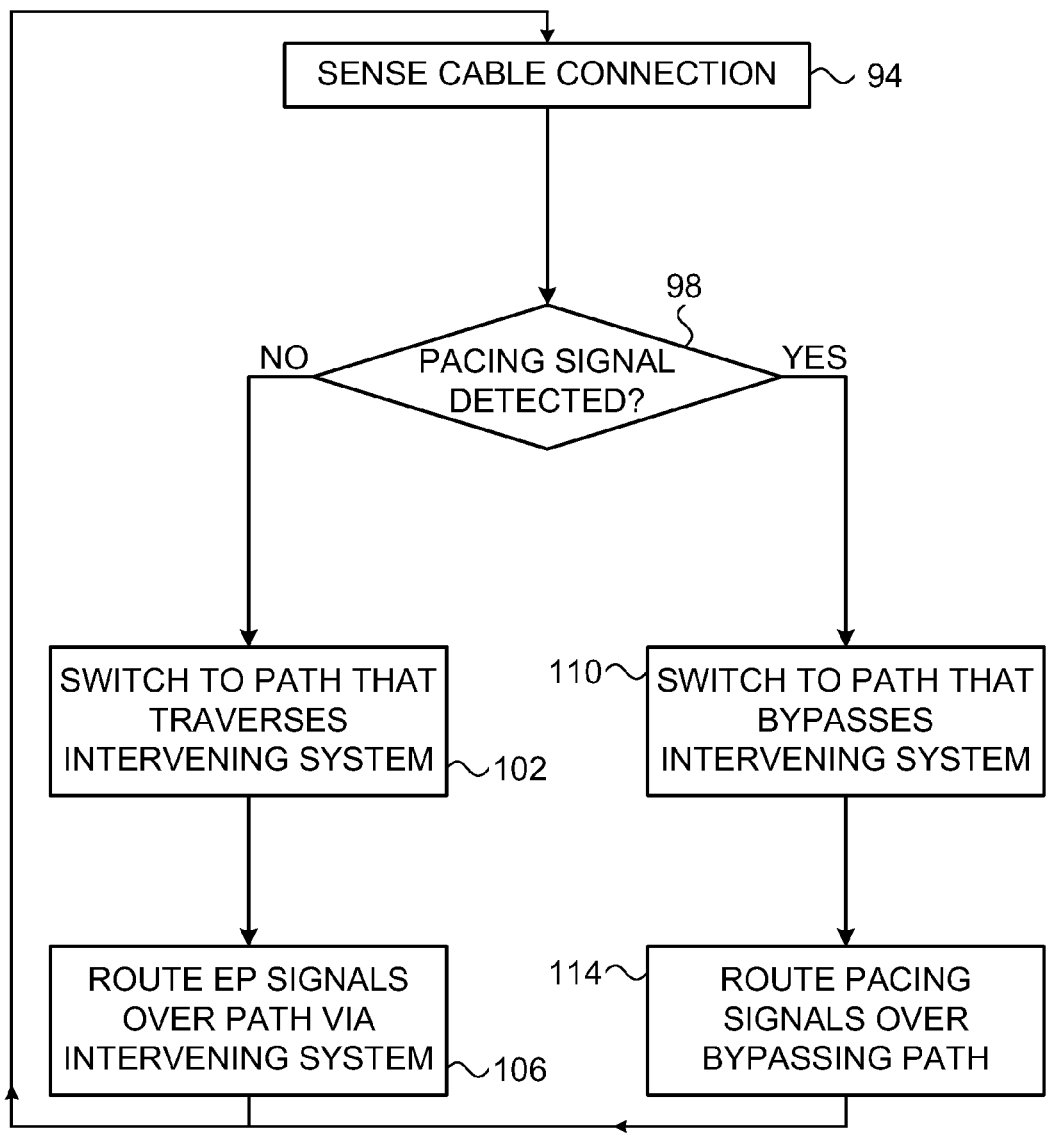
FIG. 3 is a flow chart that schematically illustrates a method for routing of pacing signals and EP signals, in accordance with an embodiment of the present invention.

FIG. 3 is a flow chart that schematically illustrates a method for routing of pacing signals and EP signals, in accordance with an embodiment of the present invention. The method begins when catheter 28 is inserted into a patient's cardiac chamber as part of an EP study procedure. The physician operates pacer 44 to apply a sequence of pacing pulses. At the same time, electrodes 36 in catheter 28 collect EP signal measurements. Both types of signals are delivered over cable connection 40.

Sensing unit 60 senses the signal voltage on cable connection 40 in order to detect the presence or absence of pacing pulses, at a sensing step 94. The sensing unit checks whether pacing pulses are present, at a signal checking step 98. If pacing pulses are not detected on cable connection 40, sensing unit 60 configures the control circuitry (switches 64 and 68 in the present example) to connect the catheter to the EP recording system over the direct path, at a direct connection step 102. The control circuitry routes the EP signals from the catheter to the EP recording system over the direct path that traverses intervening system 52, at a direct routing step 106.

If, on the other hand, a pacing pulse is detected on cable connection 40 at step 98, sensing unit 60 configures the control circuitry to connect the catheter to the EP recording system over the alternate path, at an alternate connection step 110. The control circuitry routes the pacing signal from the EP recording system to the catheter over the alternate path that bypasses intervening system 52, at an alternate routing step 114. The method loops back to sensing step 94 above, in which the sensing unit continues to sense the cable connection.

Although the embodiments described herein mainly address routing EP signals and pacing signals in the presence of catheter position tracking systems, the methods and systems described herein can also be used with other types of intervening systems.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. Apparatus, comprising:
a cardiac catheter;
an EP recording system;
a channel connecting the cardiac catheter and the EP recording system, the channel having a first path and an alternate path that bypasses the first path, the channel being configured to deliver Electro-Physiological (EP) signals from the cardiac catheter to the EP recording system and pacing signals from the EP recording system to the catheter;
a sensing unit connected to the cardiac catheter and the EP recording system over the channel, the sensing unit being configured to automatically identify time intervals during which the pacing signals are delivered; and
control circuitry connected to the sensing unit and configured to route the EP signals on the channel from the catheter to the EP recording system via the first path, to switch the channel to the alternate path during the identified time intervals, and to route the pacing signals from the EP recording system to the cardiac catheter over the alternate path.

2. The apparatus according to claim 1, wherein the sensing unit is configured to identify the time intervals by sensing the pacing pulses delivered on the channel.

3. The apparatus according to claim 2, wherein the sensing unit is configured to cause the control circuitry to route the pacing signals over the alternate path responsively to sensing the pacing signals on the channel, and to cause the control circuitry to route the EP signals via the first path responsively to sensing that the pacing signals are not present on the channel.

4. The apparatus according to claim 1, wherein the control circuitry comprises one or more switches that are controlled by the sensing unit in order to switch the channel.

5. The apparatus according to claim 4, wherein the one or more switches comprise first and second switches, and wherein the sensing unit is configured to route the pacing signals over the alternate path by opening the first switch and closing the second switch, and to route the EP signals via the first path by closing the first switch and opening the second switch.

6. The apparatus according to claim 4, wherein the sensing unit delivers pacing signals which comprise pulses having a given pulse width, and wherein the one or more switches have a switching time that does not exceed 10 percent of the given pulse width.

7. The apparatus according to claim 1, further comprising an intervening system that is detrimental to the pacing signals.

8. The apparatus according to claim 7, wherein the intervening system comprises a position tracking system that measures a position of the cardiac catheter.

9. A method in a system that includes a cardiac catheter that is connected to an Electro-Physiological (EP) recording system for recording EP signals and delivering pacing signals by a channel, routing the EP signals on the channel from the catheter to the EP recording system via a first path, comprising
delivering pacing signals from the EP recording system to the cardiac catheter;
automatically identifying time intervals during which the pacing signals are delivered;
switching the channel to an alternate path that bypasses the first path during the identified time intervals; and
routing the pacing signals from the EP recording system to the cardiac catheter over the alternate path.

10. The method according to claim 9, wherein automatically identifying time intervals comprises sensing the pacing pulses delivered on the channel.

11. The method according to claim 10, wherein switching the channel comprises routing the pacing signals over the alternate path responsively to sensing the pacing signals on the channel, and routing the EP signals via the first path responsively to sensing that the pacing signals are not present on the channel.

12. The method according to claim 9, wherein switching the channel comprises operating one or more switches.

13. The method according to claim 12, wherein the one or more switches comprise first and second switches, and wherein operating the switches comprises routing the pacing signals over the alternate path by opening the first switch and closing the second switch, and routing the EP signals via the first path by closing the first switch and opening the second switch.

14. The method according to claim 12, wherein the pacing signals comprise pulses having a given pulse width, and wherein the one or more switches have a switching time that does not exceed 10 percent of the given pulse width.

15. The method according to claim 9, further comprising an intervening system that is detrimental to the pacing signals.

16. The method according to claim 15, wherein the intervening system comprises a position tracking system that measures a position of the cardiac catheter.

* * * * *